(12) United States Patent
Hektner

(10) Patent No.: US 6,723,081 B1
(45) Date of Patent: Apr. 20, 2004

(54) CATHETER SYSTEM FOR THE DELIVERY OF A LOW VOLUME LIQUID BOLUS

(75) Inventor: Thomas R. Hektner, Medina, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/499,721

(22) Filed: Feb. 8, 2000

Related U.S. Application Data

(63) Continuation of application No. 08/982,220, filed on Dec. 1, 1997, now Pat. No. 6,050,968.

(51) Int. Cl.$^7$ .............................................. A61M 31/00
(52) U.S. Cl. ...................... 604/508; 604/510; 604/181; 604/525
(58) Field of Search .................... 604/500, 506–508, 604/510, 514–517, 264, 523, 15, 57, 59, 60, 181, 525; 606/213, 214

(56) References Cited

U.S. PATENT DOCUMENTS

| | | | | |
|---|---|---|---|---|
| 4,578,061 A | * | 3/1986 | Lemelson | 604/170.01 |
| 4,790,819 A | | 12/1988 | Li et al. | 604/59 |
| 5,306,246 A | * | 4/1994 | Sahatjian et al. | |
| 5,358,493 A | * | 10/1994 | Schweich, Jr. et al. | 604/525 |
| 5,391,183 A | | 2/1995 | Janzen et al. | 606/213 |
| 5,437,631 A | | 8/1995 | Janzen | 604/49 |
| 5,558,642 A | | 9/1996 | Schweich, Jr. et al. | 604/96 |
| 5,649,959 A | * | 7/1997 | Hannam et al. | |
| 5,702,384 A | * | 12/1997 | Umeyama et al. | |
| 5,746,728 A | * | 5/1998 | Py | |
| 5,766,157 A | | 6/1998 | Tilton, Jr. | 604/264 |
| 5,772,629 A | * | 6/1998 | Kaplan | 604/508 |
| 5,807,311 A | | 9/1998 | Palestrant | 604/43 |
| 5,820,610 A | * | 10/1998 | Baudino | |
| 5,833,658 A | | 11/1998 | Levy et al. | 604/96 |
| 5,840,061 A | * | 11/1998 | Menne et al. | 604/68 |
| 5,845,646 A | * | 12/1998 | Lemelson | 604/21 |

FOREIGN PATENT DOCUMENTS

| | | |
|---|---|---|
| EP | 0 202 658 | 4/1989 |
| WO | WO 98/10824 | 3/1998 |

* cited by examiner

Primary Examiner—Brian L. Casler
Assistant Examiner—Jeremy Thissell
(74) Attorney, Agent, or Firm—Kenyon & Kenyon

(57) ABSTRACT

A catheter system includes a catheter having a proximal end, a distal end, and a lumen extending therein. An elongate mender slidably disposed in the lumen has a distal end located proximate the distal end of the catheter. An administering tip is disposed at the distal end of the catheter and is configured to express a bolus of liquid in response to positive pressure in a distal portion of the lumen created by movement of the elongate member distally in the lumen. The present invention also includes a method of administering a liquid to a treatment site. The distal end of the catheter is transluminally positioned proximate the treatment site. The catheter is charged by placing a bolus of the liquid in a distal end of the lumen between a distal tip of the catheter and a distal end of the elongate member. The elongate member is then moved distally within the lumen to express the bolus from the distal end of the catheter.

22 Claims, 4 Drawing Sheets

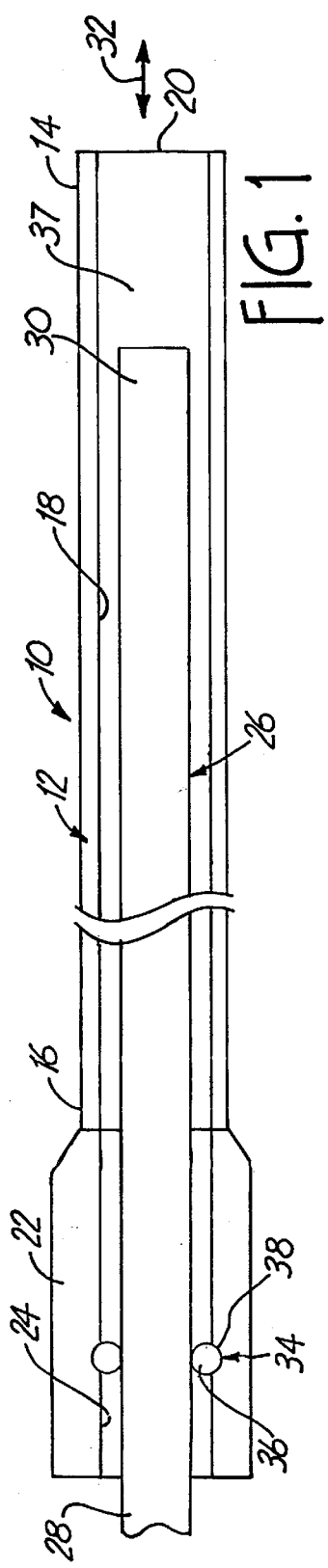
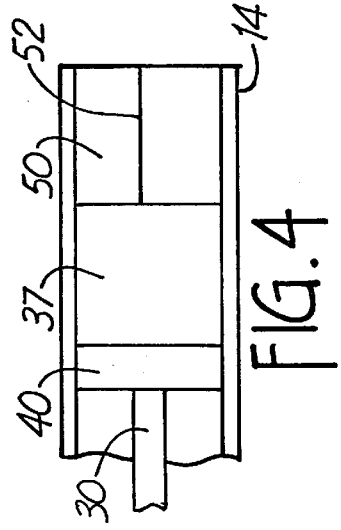
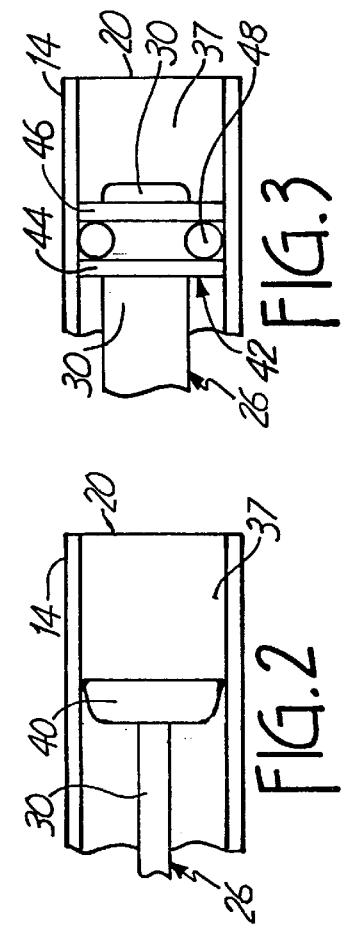
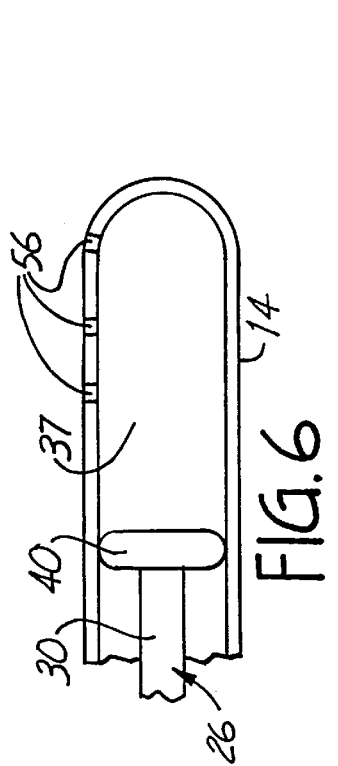
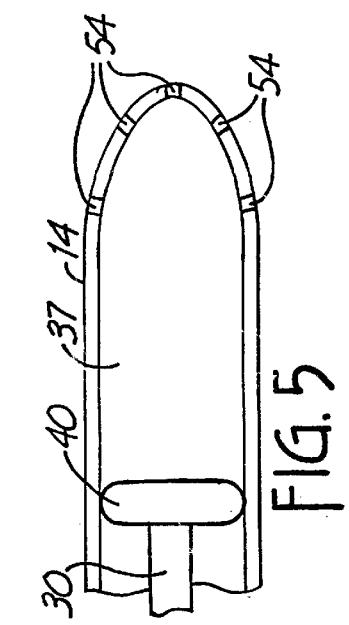

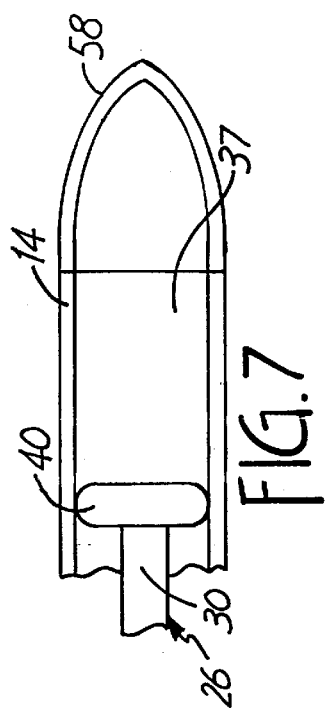
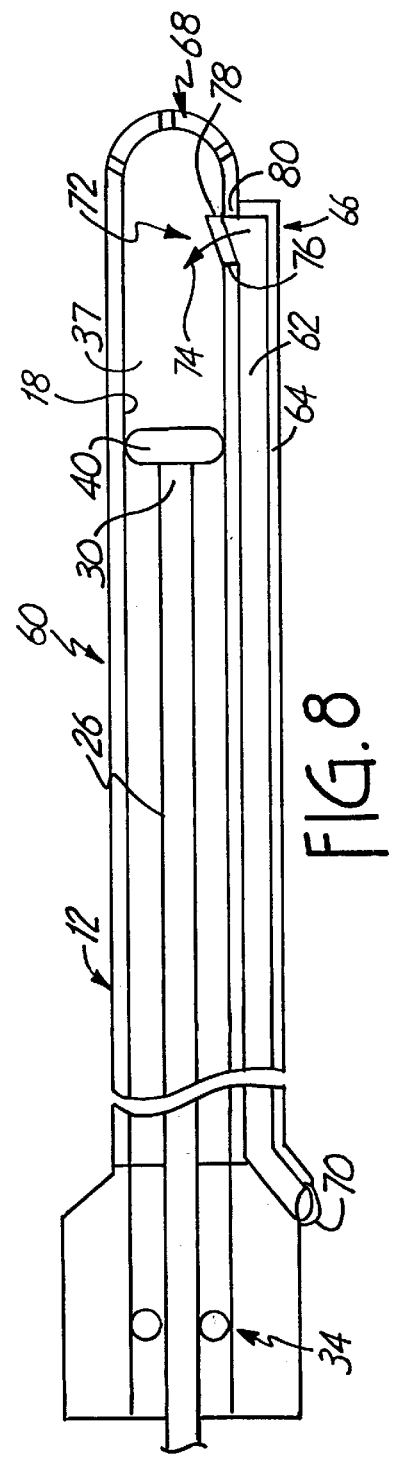
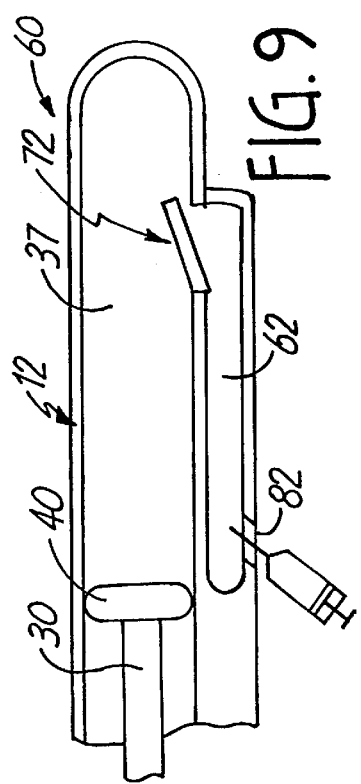

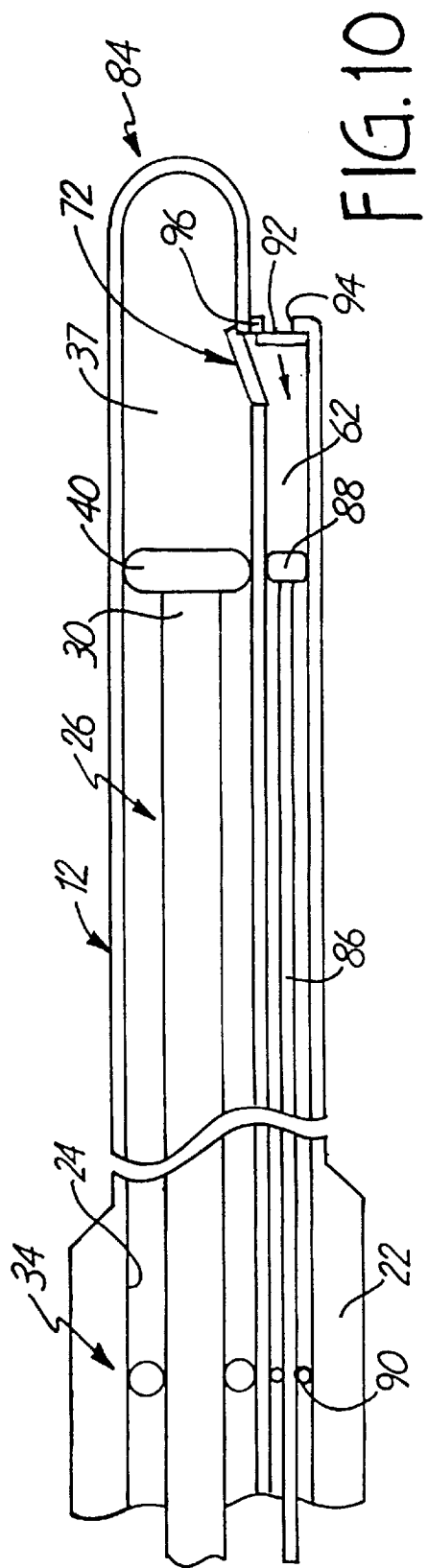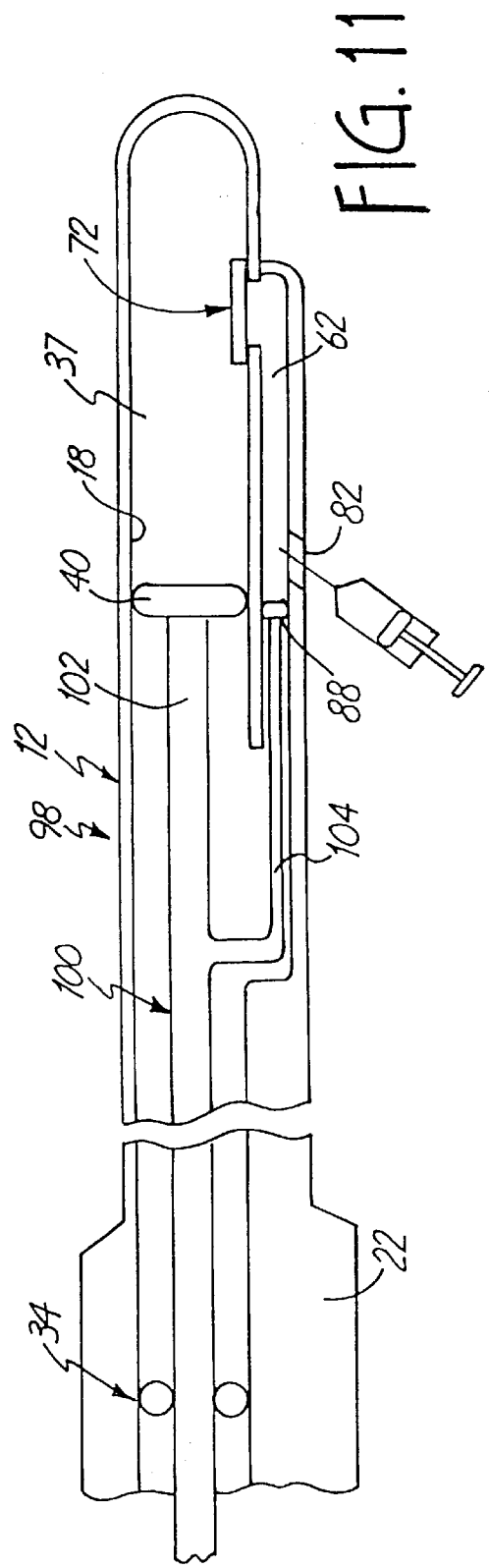

CATHETER SYSTEM FOR THE DELIVERY OF A LOW VOLUME LIQUID BOLUS

CROSS-REFERENCE TO RELATED APPLICATION

This application is a continuation of U.S. Ser. No. 08/982,220, filed Dec. 1, 1997 and which issued as U.S. Pat. No. 6,050,968.

INCORPORATION BY REFERENCE

Reference is made to the following patent applications which are hereby fully incorporated by reference:

U.S. patent Ser. No. 08/308,025, filed on Sep. 16, 1994 entitled "BALLOON CATHETER WITH IMPROVED PRESSURE SOURCE", now U.S. Pat. No. 5,545,133.

U.S. patent Ser. No. 08/586,514 filed on Jan. 16, 1996 entitled "BALLOON CATHETER WITH IMPROVED PRESSURE SOURCE", now U.S. Pat. No. 5,695,468

U.S. patent Ser. No. 08/619,375 filed on May 21, 1996 entitled "BALLOON CATHETER WITH IMPROVED PRESSURE SOURCE", now U.S. Pat. No. 5,728,064 and U.S. patent Ser. No. 08/812,390 filed on Mar. 5, 1997 entitled "BALLOON CATHETER WITH IMPROVED PRESSURE SOURCE, now U.S. Pat. No. 5,785,685.

All of the above-referenced patent applications are assigned to the same assignee as the present application.

BACKGROUND OF THE INVENTION

The present invention deals with catheters. More specifically, the present invention deals with delivery of a small bolus of liquid with a catheter.

A wide variety of different mechanisms and techniques have been developed in order to treat coronary disease. However, such techniques and devices are typically drawn to the physical manipulation of biological tissues, such as heart tissue, or other vascular tissue within the vascular system.

For example, some treatment techniques are drawn to the physical removal or dilation of restrictions (stenoses and total occlusions) in the vasculature. Techniques for dealing with this type of disease have included percutaneous transluminal coronary angioplasty (PTCA) in which an angioplasty balloon catheter is inserted into the body via the femoral artery and positioned across a restriction in an artery. The balloon is inflated to widen the restriction and restore blood flow to portions of the heart muscle previously deprived of oxygenated blood. Implantation of stents using PTCA is also a common technique for opening an arterial restriction.

Another technique for dealing with vascular disease includes coronary artery bypass graft (CABG) procedures. Such procedures typically include the placement of a graft at a desired location in the vasculature to supplement blood flow to the area previously deprived of blood for (or provided with reduced blood flow) due to the vascular restriction. One common type of CABG procedure involves placement of a saphenous vein graft (SVG) between the ascending aorta proximal of the restriction, and a region in the restricted vessel distal of the restriction.

Another technique for dealing with vascular disease includes an atherectomy procedure. In an atherectomy procedure, an atherectomy device is placed in the vasculature proximate the restriction. The atherectomy device is deployed to physically cut away, abrade, or otherwise physically remove, the occlusive material from the restricted vessel. The portions of the restriction which are severed by the atherectomy device are subsequently removed by aspiration, or by another suitable means.

Another technique called transluminal myocardial revascularization is also receiving attention in the medical community as an acceptable therapy.

Various drug therapies have also been developed. Such therapies have been used in place of, and in conjunction with, the above mentioned therapies under certain circumstances. For example, during grafting procedures, it may be desirable to deliver drugs to the graft site which inhibit the formation of thrombus. In addition, some drug therapies have been developed which involve the delivery of drugs directly to the heart tissue. With recent advancements in the pharmaceutical industry, other drug therapies have also become desirable. Some such recent pharmaceutical developments include the development of gene therapy drugs, such as growth factors.

A transluminal technique for delivering the drugs, along with the various types of known positioning and visualization techniques commonly used with transluminal treatments, can be highly desirable. The drug therapies typically require site-specific administration of the drug. Transluminal techniques can be effectively used to deliver a liquid material to a selected site in the vasculature.

However, drug therapies, can be prohibitively expensive. For example, newly developed drugs are commonly extremely expensive and can only be administered in any pragmatic fashion in very low volumes. Typically, such drugs only need to be administered to the vascular site being treated. However, there is no technique available to date by which the site to be treated can be accessed transluminally with a catheter and which enables only a very small quantity of drug to be delivered from the distal tip of the catheter to the treatment site.

Rather, conventional transluminal drug delivery catheters require a proximal infusion device which is connected to a proximal end of the infusion catheter and which is used to pressurize a fluid or infusate which contains the drug to be delivered. The catheter is filled with the infusate and the drug is administered at the distal tip of the infusion catheter (upon pressurization of the infusate) after the catheter is inserted and properly positioned. While the internal volume of such infusion catheters is typically small, it is still much too large to make drug delivery with extremely expensive drugs practical.

SUMMARY OF THE INVENTION

The present invention is drawn to the delivery of a low volume bolus of drug or other treatment material to the myocardium, a vessel, or any other organ or area for which transluminal access is desirable. For example, antiarrhythmia drugs may be injected into the myocardium using the present invention for electrophysiological therapy. Also, growth factors and other gene therapy substances can be injected into the myocardium for myocardial revascularization.

The catheter system includes a catheter having a proximal end, a distal end, and a lumen extending therein. An elongate member slidably disposed in the lumen has a distal end located proximate the distal end of the catheter. An administering tip is disposed at the distal end of the catheter and is configured to express a bolus of liquid in response to positive pressure in a distal portion of the lumen created by movement of the elongate member distally in the lumen.

The present invention also includes a method of administering a liquid to a treatment site. A catheter, having a proximal end, a distal end and a lumen extending therein, as well as an elongate member, slidably disposed in the lumen, are provided. The distal end of the catheter is transluminally positioned proximate the treatment site. The catheter is charged by placing a bolus of the liquid in a distal end of the lumen between a distal tip of the catheter and a distal end of the elongate member. The elongate member is then moved distally within the lumen to express the bolus from the distal end of the catheter.

Also, the present device should not be limited to implementation using only conventional catheters per se, but also contemplates any steerably, maneuverable syringe structure. Thus, the term catheter should be construed to include both conventional catheters and elongate, maneuverable syringe barrel structures suitable for maneuvering, manipulation, tracking and steering within a vessel.

The catheter system can be navigated through several lumens and cavities within the body. Intravascular access by the femoral, brachial and radial arteries is contemplated for accessing target sites within the heart or peripheral vasculature. Alternatively, the catheter may be navigated into the ventricles of the heart by way of the aorta for direct treatment of the heart muscle (myocardium). Yet another alternative for accessing the heart chamber is via the vena cava. Lastly, nonvascular ducts or lumens within the body can be accessed for drug delivery such as for cancer treatment.

BRIEF DESCRIPTION OF THE DRAWINGS

FIG. 1 is a side sectional view of a catheter system in accordance with one preferred embodiment of the present invention.

FIG. 1A illustrates an embodiment of a catheter system of the present invention including a guidewire lumen having a guidewire extending therethrough.

FIG. 2 is an enlarged side sectional view of second embodiment of a distal tip of the catheter system in accordance with the present invention.

FIG. 3 is an enlarged view of the distal end of a catheter system in accordance with another preferred embodiment of the present invention.

FIG. 4 is an enlarged side sectional view of another embodiment of a distal tip of the catheter system in accordance with the present invention.

FIG. 5 is an enlarged side sectional view of another embodiment of a distal tip of the catheter system in accordance with the present invention.

FIG. 6 is an enlarged side sectional view of another embodiment of a distal tip of the catheter system in accordance with the present invention.

FIG. 7 is an enlarged side sectional view of another embodiment of a distal tip of the catheter system in accordance with the present invention.

FIG. 8 is a side sectional view of another embodiment of a catheter system in accordance with the present invention.

FIG. 9 is a side sectional view of the catheter system of FIG. 8, with a modified liquid reservoir configuration.

FIG. 10 is a side sectional view of a catheter system in accordance with one aspect of the present invention, deploying a two piston arrangement.

FIG. 11 is a side sectional view of a catheter system in accordance with one aspect of the present invention utilizing a bifurcated piston configuration.

DETAILED DESCRIPTION OF THE PREFERRED EMBODIMENTS

Figure 12:
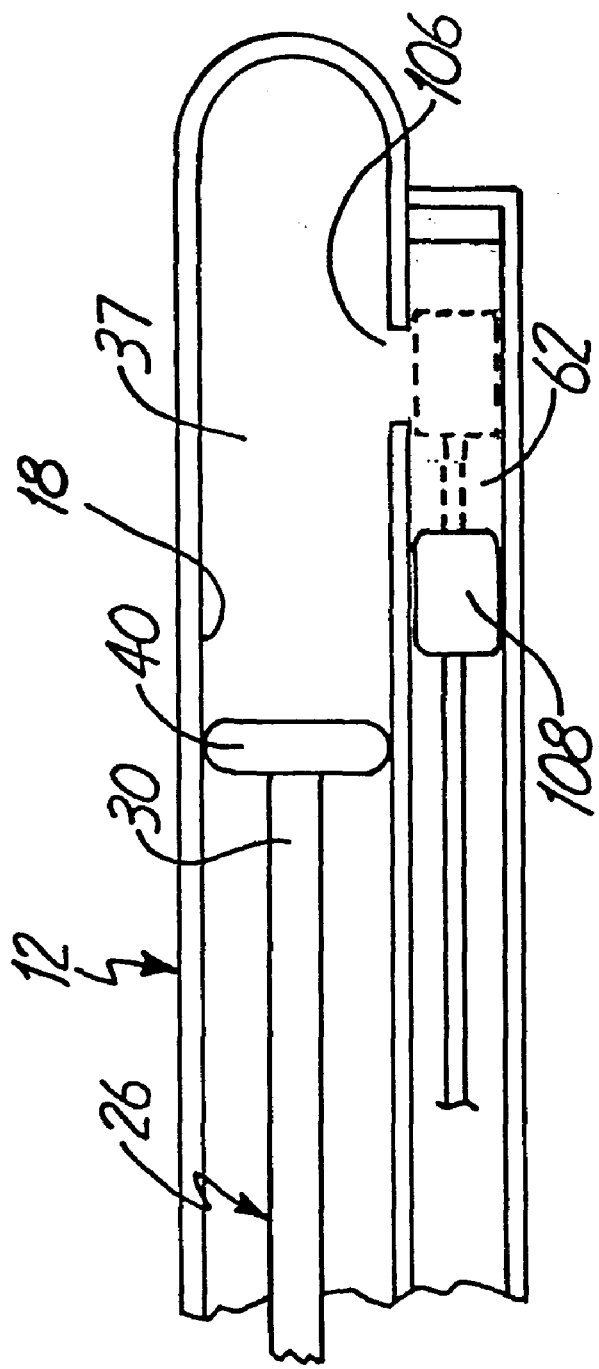
FIG. 12 is a side sectional view of a catheter system in accordance with one aspect of the present invention utilizing a valve and engageable valve seat configuration.

FIG. 1 is a side sectional view of a catheter system 10 in accordance with one preferred embodiment of the present invention. Catheter system 10 includes catheter 12 having a distal end 14 and a proximal end 16 and a lumen 18 running therethrough. In the embodiment shown in FIG. 1, distal end 14 is simply an open end providing distal opening 20, and proximal end 16 is coupled to proximal manifold 22 in any known conventional manner.

Manifold 22 preferably has a lumen 24 extending therethrough which is coaxial with lumen 18. Lumen 24 is also preferably in fluid communication with lumen 18.

System 10 also preferably includes piston rod 26. Piston rod 26 is preferably an elongate member which extends from a proximal end 28 (which preferably extends to a region proximal of manifold 22) to a distal end 30 which is preferably proximate distal end 14 of catheter 12. Piston rod 26 preferably has an outer diameter which is just smaller than the inner diameter of lumen 18. Also, piston rod 26 is preferably slidably disposed within lumen 18 such that piston rod 26 can slide in a direction generally parallel to the longitudinal axis of catheter 18, in the direction indicated by arrow 32.

Piston rod 26 is supported for reciprocal movement within lumen 18 by virtue of its outer dimensions relative to the inner dimensions of lumen 18, and also be seal arrangement 34. Seal arrangement 34 is preferably an o-ring type seal which fluidically seals the interior of lumen 18 from the exterior of system 10 through the proximal end of manifold 22. Thus, seal arrangement 34 preferably includes an o-ring 36 which is disposed within a generally annular depression or recess 38 formed in lumen 24 of manifold 22. O-ring 36 is preferably formed of a conventional sealing material, such as silicon rubber, and is secured in annular recess 38 utilizing a suitable adhesive.

The distal end 30 of rod 26, when positioned as shown in FIG. 1, preferably cooperates with the inner periphery of the distal end 14 of catheter 12 to form a bolus chamber 37 for containing a bolus of treatment material. The treatment material contained in chamber 37 can be a drug, growth factors, gene therapy materials, radioactive fluid for restenosis or cancer treatment, clot dissolution agent, or any other desired fluid or liquid material. Also, the material can be injected by high pressure, at high velocity, to mechanically break up clots. As described later in the specification, material delivered by system 10 is administered to a desired site in the body by reciprocation of rod 26 in lumen 18.

The proximal end 28 of piston rod 26 is preferably formed in any suitable manner which allows the user to easily grasp and reciprocate rod 26 within lumen 18. For example, in the above-identified patent applications which are hereby fully incorporated by reference, a number of different proximal grasping and manipulating members are disclosed. In one arrangement, a threadable connection is provided between proximal end 28 of rod 26 and manifold 22. In this way, the user can rotate rod 26 to cause either proximal or distal reciprocal movement within lumen 18. In another preferred embodiment, a release mechanism is provided such that the threadable engagement between rod 26 and manifold 22 can be disengaged to simply push or pull rod 26 for quicker longitudinal movement of rod 26. Then, for finer adjustment of rod 26, the threaded engagement is re-engaged and rod 26 is rotated to accomplish longitudinal movement. Further, in the references which are incorporated herein, various grasping members are provided to facilitate grasping and manipulation of rod 26 by the user. Also, electromechanical (e.g., solenoid) actuation of rod 26 can also be used.

In any case, in a preferred embodiment, catheter 12 is preferably formed of a suitable material to track through desired vasculature and to access a treatment site in the body. Therefore, in operation, prior to being inserted in the vasculature, catheter 12 is preferably filled with a solution, such as saline, such that all areas between rod 26 and the inner wall of lumen 18 are filled with the liquid solution to eliminate any dead space in lumen 18. A therapeutic drug or other fluid material is then loaded into the distal end 14 of catheter 18. This may be done, for example, by moving rod 26 to a position in which its distal end 30 is approximately coterminous with the opening 20 in lumen 18 of catheter 12. Then, distal end 14 of catheter 12 is placed in the liquid solution to be introduced into the vasculature, and rod 26 is withdrawn a desired distance proximally. Withdrawing rod 26 proximally creates a vacuum in chamber 37 of catheter 12 and thus draws some of the liquid solution to be introduced into chamber 37 of catheter 12. In one preferred embodiment, visual indicia are provided at the proximal end 28 of rod 26 to indicate to the user the total volume of liquid solution which has been drawn into the distal end 14 of catheter 12 based on proximal withdrawal of rod 26.

After catheter 12 has been charged with the treatment solution, distal end 14 of catheter 12 is advanced through the vasculature and positioned proximate a desired treatment site. This can be accomplished in any number of known manners. For example, the distal tip 14 of catheter 12 can be provided as a cutting tip which can be used to pierce the skin and enter the desired vessel. Further, a separate cutting device can be provided which is used in conjunction with (e.g., over the top of) catheter 12 to introduce catheter 12 into the desired vessel. Still further, conventional guidewire or guide catheter assemblies can be used in conjunction with catheter 12 to guide catheter 12 to a desired location in the vasculature. Use of a guidewire with catheter 12 is preferably accomplished by either providing a separate lumen in catheter 12, separate from lumen 18, over which catheter 12 can track the guidewire. FIG. 1A illustrates a catheter 12A including a separate guidewire lumen 18-1 having a guidewire 18-2 inserted therethrough to track the catheter from a percutaneous insertion position to a treatment site. Alternatively, catheter 12 can be formed as a single-operator-exchange catheter which includes a distal guidewire tube for tracking over the guidewire. Such arrangements are more fully discussed in the above-referenced U.S. patent applications.

In any case, distal end 14 of catheter 12 is advanced under suitable visualization, or according to other positioning techniques, until it resides proximate the site to be treated. Once appropriately positioned, the user advances rod 26 distally such that the distal end 30 of rod 26 creates a positive pressure within chamber 37 of lumen 18 at the distal end 14 of catheter 12. This positive pressure forces the liquid treatment material out the distal opening 20 in catheter 12 so that it is administered at the desired.

In a preferred embodiment, the volume of the chamber 37, which is defined by the interior periphery of catheter 12 and the distal tip of rod 26, is preferably less than or equal to approximately 1 ml. Thus, it can be seen that the present invention can be used to directly administer a very low volume bolus of drug or other therapeutic material directly to a desired treatment site within the body, using a transluminal technique.

The specific materials used in implementing catheter system 10 can be any suitable, and commercially available materials. For example, manifold 22 is preferably made of an injection molded polycarbonate. Recess 38 within which o-ring 36 resides preferably has approximately a 0.123 inch diameter recess formed in manifold 22, and the inner diameter of lumen 24 in manifold 22 is preferably approximately 0.042 inches. Catheter 12 can be formed of several sections, or only a single section. Catheter 12 can also be made of any suitable materials, depending on the performance characteristics desired. For example, catheter 12 can be made of an extruded polymer tube, stainless steel hypotube, or a composite material such as stainless steel braid encased in polyimide. To impart different characteristics along its length, catheter 12 may incorporate changes in diameter or combine different constructions. For example, catheter 12 may have a composite proximal section combined with a polymer distal section. Other suitable configurations can be used as well.

Rod 26 is preferably made of a stainless steel wire surrounded by a Kynar™ tube. The stainless steel wire preferably has a diameter of approximately 0.019 inches and a length of about 50 inches. The tube surrounding the wire preferably has an outside diameter of approximately 0.038 inches and an inside diameter of 0.020 inches. When fully actuated in the distal direction, rod 26 preferably extends such that its distal end 30 is co-terminus with the distal end 14 in catheter 12. Positive stops (not shown) can optionally be provided at the distal end 14 of catheter 12 to limit the distal movement of rod 26.

Generally, connections between the various polymer components may be made utilizing suitable grade medical adhesives or thermal bonds which are well known to those skilled in the art. Connections between metallic components are preferably made, for example, by utilizing solder, by brazing, welding, or other suitable techniques.

FIG. 2 is an enlarged view of a distal end portion 14 of catheter 12. Some items shown in FIG. 2 are similar to those shown in FIG. 1, and are correspondingly numbered. However, FIG. 2 illustrates that, rather than rod 26 simply having distal end 30, a plunger 40 is coupled to distal end 30 of rod 26. Plunger 24 has an outer diameter which is approximately the same as, or just smaller than, the inner diameter of lumen 18. Thus, when rod 26 is actuated in the distal direction, plunger 40 and rod 26 act much like a conventional syringe in that the distal chamber 37 defined by the distal end 14 of catheter 12 and plunger 40, is pressurized. This forces the bolus of treatment material out through the distal opening 20 in catheter 12. However, since plunger 40 is provided, the outer periphery of the remainder of actuating rod 26 need not be approximately the same as, or just smaller than, the interior periphery of lumen 18. Instead, it can be much smaller. This significantly reduces the frictional forces acting on rod 26 as it is reciprocated within lumen 18. It should be noted that plunger 40 can be a separate member attached to the distal end 30 of rod 26, or it can be formed integrally with rod 26 simply by broadening out the distal end 30 of rod 26.

FIG. 3 is another enlarged view of the distal end of rod 26. Some items are similar to those shown in FIG. 2, and are similarly numbered. However, rather than having simply plunger 40, the embodiment shown in FIG. 3 includes plunger head 42. Plunger head 42 includes a pair of discs 44 and 46 which are mounted about the outer periphery of the distal end 30 of rod 26. The discs 44 and 46 are preferably separated by an o-ring 48 formed of silicone or other suitable material and sized to fluidically seal lumen 18. Discs 44 and 46 are also preferably formed of silicon rubber material, or other suitable material, or can be formed integrally with rod 26.

FIG. 4 is an enlarged side sectional view of the distal end 14 of catheter 12 in accordance with another aspect of the present invention. Some items are similar to those shown in FIG. 2 and are correspondingly numbered. However, rather than simply having a distal opening 20 in the distal end 14 of catheter 12, FIG. 4 illustrates that a separable seal 50 is provided in distal end 14. Separable seal 50 preferably includes a rubber or polymer material inserted into the distal end 14 of catheter 12 and connected thereto with a suitable adhesive.

Separable seal 50 preferably includes a seam 52 therein. Seam 52 is simply formed by the abutment of the surfaces of seal 50 against one another, but those portions are not adhesively or otherwise sealed to one another (other than through friction). This arrangement allows the introduction of a conventional, small diameter, needle which is attached to a syringe containing the treatment solution into the distal end 14 (and hence chamber 37) of catheter 12, and through seam 52. Thus, the treatment solution can be injected into chamber 37 of catheter 12, as plunger 40 is withdrawn in the proximal direction to draw the treatment solution therein.

Once the distal end 14 of catheter 12 is placed at the treatment site in the vasculature, distal actuation of rod 26 causes plunger 40 to create a pressure behind seal 50 causing seal 50 to separate at seam 52 and thus release the treatment solution at the desired location. In another preferred embodiment, seal 50 is a rolling diaphragm type of seal, or another suitable type of seal configuration.

FIG. 5 is an enlarged side sectional view of distal end 14 of catheter 12 in accordance with another aspect of the present invention. Similar items are similarly numbered to those shown in previous figures. However, FIG. 5 illustrates that the distal tip of catheter 12 is provided with a needle having a plurality of apertures 54 therein. Apertures 54 allow the treatment solution 37 to be withdrawn into the distal end 14 of catheter 12, and to be forced out through the distal end thereof.

FIG. 6 illustrates yet another embodiment in accordance with the present invention. FIG. 6 is similar to FIG. 5 except that, rather than having uniformly spaced apertures 54 at the distal tip of catheter 12, the distal tip or nozzle region is provided with side ports 56 which allow the treatment solution in chamber 37 to be directionally administered in the direction in which side ports 56 are disposed.

FIG. 7 illustrates another preferred embodiment in accordance with the present invention. Similar items are similarly numbered to those shown in previous figures. However, the distal end of catheter 12, rather than being provided as a solid member with apertures therein, is provided as a porous needle portion 58. Porous needle portion 58 can be provided as a microporous membrane, as a selectively porous membrane, or as any other suitable porous or capillary type material, suitable for the introduction of treatment solution from chamber 37 to the treatment site.

FIG. 8 is a side sectional view of a catheter system 60 in accordance with another preferred embodiment of the present invention. Some items are similar to those shown in FIGS. 1–7, and are similarly numbered. However, catheter 12 is also provided with a treatment fluid reservoir 62 defined by wall 64 which is preferably arranged about an exterior portion of catheter 12. Reservoir 62 extends from a distal end 66 which is arranged just proximal of administration tip (or nozzle) 68, to a proximal end 70 which is provided with a suitable fitting for receiving the treatment solution.

In operation, the treatment solution is preferably injected, using a standard syringe, through proximal portion 70 of reservoir 62. A flapper valve 72 is preferably provided at distal end 66 of reservoir 62 to fluidically separate lumen 18 in catheter 12 from reservoir 62. In the preferred embodiment, flapper valve 72 is arranged such that it pivots generally in a direction indicated by arrow 74 and is hingedly attached by hinge 76 to the wall of catheter 12. Flapper valve 72 has a distal end 78 which engages a positive stop 80 on the inside of lumen 18 of catheter 12.

Therefore, when plunger 40 is withdrawn proximally, this creates a vacuum or low pressure area within chamber 37, relative to reservoir 62. This causes flapper valve 72 to lift upwardly to allow fluid to escape from reservoir 62 into chamber 37. Then, when plunger 40 is advanced distally, this creates a high pressure region in lumen 18 relative to reservoir 62 so that flapper valve 72 closes and the distal end 78 of flapper valve 72 abuts positive stop 80.

As plunger 40 continues to be advanced distally, the treatment solution in chamber 37 is passed through administering tip 68 to the desired site. In the preferred embodiment, administering tip 68 is provided with very small apertures, or pores, or valved openings, such that a greater pressure differential is required between the interior lumen 18 and the exterior of catheter 12 to cause liquid material to pass through administering tip 68 than is required to lift flapper valve 72. Therefore, as plunger 40 is withdrawn proximally, flapper valve 72 opens to allow the treatment material in chamber 62 to enter lumen 18, but no fluid, or very little fluid, is drawn into lumen 18 from outside catheter 12. Then, as plunger 40 is advanced distally, flapper valve 72 closes and a great enough pressure is built within chamber 37 to cause the treatment material to pass through administering tip 68 to the desired position.

It will thus be appreciated that the embodiment disclosed in FIG. 8 allows the user to position distal tip 14 of catheter 12 at the desired location within the body before chamber 37 is charged with the bolus of treatment material to be injected at the treatment site.

FIG. 9 shows another embodiment of the distal end 14 of catheter 12 in catheter system 60. Similar items are similarly numbered to those shown in FIG. 8. However, rather than providing reservoir 62 extending all the way from distal end 66 thereof to proximal end 70 thereof, reservoir 62 is maintained only at a distal portion of catheter 12. Reservoir 62 is also provided with a suitable introduction valve 82 which can preferably be used in conjunction with a conventional syringe, to introduce the bolus of treatment material into reservoir 62. By not requiring reservoir 62 to extend all the way to the proximal end 70, the internal volume of reservoir 62 can be kept very small. This facilitates utilizing only a needed volume of treatment material. No extra material is required to fill the internal volume of reservoir 62, since that volume is so small.

FIG. 10 shows another preferred embodiment of the catheter system 84 in accordance with the present invention. Catheter system 84 is similar to catheter system 60 shown in FIG. 8, and similar items are similarly numbered. However, catheter system 84 includes a modified form of treatment reservoir 62. Rather than terminating in its proximal area at proximal end 70, the proximal end of reservoir 62 in catheter system 84 extends all the way through proximal manifold 22 in the same fashion as lumen 24. Also, reservoir 62 is provided with a reciprocally mounted rod 86 and plunger 88. Further, rod 86 is sealably mounted within manifold 22 by seal configuration 90 which is similar to seal configuration 34 discussed with respect to FIG. 1. The proximal ends of rods 26 and 86 can optionally be either connected to one another, or separate from one another for separate actuation by the user.

In any case, in order to introduce the bolus of treatment material into reservoir 62, rod 86 and plunger 88 are advanced to the distal-most actuation point in which they abut a second flapper valve arrangement 92. Flapper valve 92 is biased to normally close an aperture 94 against an inner portion 96 of the distal end of reservoir 62. Then, the distal tip 14 of catheter 12 and reservoir 62 are placed in the drug solution to be administered. Rod 86 and plunger 88 are then withdrawn distally a desired amount such that flapper valve 92 opens to allow the fluid to be administered to enter reservoir 62 through aperture 94. When the distal tip 14 of catheter 12 is appropriately positioned in the vasculature, rod 86 and plunger 88 are then advanced distally to charge catheter 12 by introducing the material to be administered from reservoir 62, through flapper valve arrangement 72, and into chamber 37 in catheter 12. Once charged, catheter 12 is ready to administer the treatment solution. Thus, the user advances rod 26 and plunger 40 such that the bolus of treatment solution is injected from chamber 37 through the administering tip of catheter 12 to the desired site.

FIG. 11 shows another catheter system 98 in accordance with another preferred embodiment of the present invention. Similar items are similarly numbered to those shown in previous figures. Catheter system 98 is similar to catheter system 84 and similar items are correspondingly numbered. However, rather than providing two rods 26 and 86, as in FIG. 10, catheter system 98 includes bifurcated rod 100. Bifurcated rod 100 includes first leg portion 102 which is connected to plunger 40 and which resides within lumen 18 of catheter 12. Bifurcated rod 100 also includes second leg portion 104 which is connected to plunger 88 and lies in reservoir 62. Catheter system 98 shown in FIG. 11 is also preferably provided with a valve arrangement similar to valve arrangement 82 shown in FIG. 9 by which the treatment material is inserted into reservoir 62.

In the embodiment shown in FIG. 11, the treatment material is simultaneously introduced from reservoir 62 into chamber 37 distal of plunger 40, and it the bolus of material is injected at the desired site, as the user advances bifurcated rod 100 distally. Plunger 82 causes high pressure in reservoir 62 to move the bolus of treatment material from reservoir 62 into chamber 37 distal of plunger 40. At the same time, plunger 40 causes high pressure to be developed in chamber 37 such that the bolus of material is advanced through the administering tip to the desired site.

FIG. 12 is similar to FIGS. 10 and 11, and similar items are similarly numbered. However, reservoir 62 is provided with different valve arrangements. Rather than flapper valve 72, a simple aperture 106 is provided between reservoir 62 and lumen 18. A plunger 108 is sized to completely cover aperture 106 when it is advanced to its distal most position (shown in phantom in FIG. 12). Thus, the operator can advance plunger 108 within reservoir 62 to charge lumen 18 with a bolus of material. The operator can, either simultaneously or separately, advance plunger 40 to administer the material through the tip of the catheter, once chamber 37 has been charged with the bolus.

Thus, it can be seen that the present invention provides a number of advantages over prior art infusion techniques.

The present invention can be utilized to transluminally access a site to be treated within the body. The present invention can also be utilized to administer a therapeutic solution, or any desired solution, at that site. Further, the present invention can be utilized to administer only a very small volume bolus of material, preferably less than 1 milliliter at the site. This allows the pragmatic administration of even very expensive drugs in an efficient and accurate manner.

It should also be noted, of course, that the distal tip of the catheter can be arranged to provide any sort of nozzle configuration. The distal tip can be valved, it can have apertures uniformly distributed thereabout, it can have apertures directionally distributed thereabout, and it can have apertures which provide desired injection or dispersion characteristics.

Although the present invention has been described with reference to preferred embodiments, workers skilled in the art will recognize that changes may be made in form and detail without departing from the spirit and scope of the invention.

What is claimed is:

1. A method of administering a fluid to a treatment site in a human body, the method comprising:

provide a catheter comprising: a flexible elongated catheter shaft having a proximal end, a distal end, and a lumen extending therein; a flexible elongate member, slideably disposed in the lumen, and having a distal end spaced from a distal end of the lumen in a retractable position to form a distal bolus chamber and slideable in the lumen to express a bolus; and a reservoir having a distal portion located proximate the bolus chamber and being configured to provide fluid communication between the reservoir and the bolus chamber;

charging the catheter by placing a bolus of the fluid in the bolus chamber;

inserting the distal end of the charged catheter having the bolus of fluid in the bolus chamber into a vascular vessel;

intravascularly steering the charged catheter through the vascular vessel using a visualization of a position of the charged catheter in the vascular vessel to advance the distal end of the charged catheter proximate to a treatment site; and grasping the proximal end of the flexible elongate member and sliding the flexible elongate member distally within the lumen to express the bolus of fluid from the distal end of the catheter into the vascular vessel.

2. The method of claim 1 wherein charging the catheter comprises:

grasping the proximal end of the elongate member and moving the elongated member proximally within the lumen; and receiving the bolus in the distal end of the lumen.

3. The method of claim 1 wherein the step of intravascularly steering the charged flexible catheter to the treatment site comprises:

positioning the distal end of the catheter proximate the myocardium.

4. The method of claim 1 wherein the step of intravascularly steering the charged flexible catheter to the treatment site comprises: positioning the distal end of the catheter proximate to the treatment site in the vasculature.

5. The method of claim 1 wherein the step of intravascularly steering the charged flexible catheter to the treatment site comprises:
   positioning the distal end of the catheter proximate to a body organ.

6. A cardiovascular catheter system for delivering a bolus of fluid to a cardiovascular treatment site in a human body, comprising:
   a flexible intravascular transluminal catheter including an elongated intravascular catheter shaft having a proximal end, a distal end, and a lumen extending therein;
   a flexible elongate member, slideably disposed in the lumen of the catheter shaft, and having a distal portion locatable proximate the distal end of the catheter shaft and slideable therealong to form a distal bolus chamber proximate to a distal end of the catheter configured to express the bolus of fluid in response to positive pressure created by movement of the elongate member distally in the lumen and configured to charge the bolus chamber with a bolus of fluid by retraction of the elongate member in the lumen and the catheter shaft and the elongate member being adapted for percutaneous insertion into a body lumen and adapted to transluminally tract through the body lumen from a percutaneous insertion position to the cardiovascular treatment site to express the bolus of fluid in the body lumen in response to movement of the elongate member;
   a guidewire lumen extending along the catheter shaft; and
   a guidewire extending through the guidewire lumen to transluminally tract the catheter to the cardiovascular treatment site inside the body lumen.

7. The catheter system of claim 6 wherein the distal portion of the elongate member is sealably engaged relative to an inner wall surrounding the lumen of the catheter shaft.

8. The catheter system of claim 6 and comprising an administering tip at the distal end of the catheter including an opening for expressing the bolus of fluid.

9. The catheter system of claim 8 wherein the administering tip comprises:
   a needle tip having at least one aperture therein.

10. The cardiovascular system of claim 6 wherein the catheter shaft includes a variable stiffness construction along a length thereof to transluminally tract from the percutaneous insertion position through the body lumen to the cardiovascular treatment site.

11. A catheter comprising:
   a flexible elongated catheter shaft having a proximal end, a distal end and a lumen extending therealong;
   a flexible elongate member slideably disposed in the lumen of the catheter shaft and having a distal end spaced from a distal end of the lumen in a retractable position to form a distal bolus chamber and slideable in the lumen to express a bolus; and
   a reservoir having a distal portion located proximate the bolus chamber and being configured to provide fluid communication between the reservoir and the bolus chamber.

12. The catheter system of claim 11 wherein the reservoir includes an aperture therein in liquid communication with the bolus chamber.

13. The catheter system of claim 11 wherein the reservoir has a proximal portion proximate a proximal end of the catheter, the proximal portion including an aperture configured to receive the bolus.

14. The catheter of claim 11 and comprising a valve between the reservoir and the bolus chamber.

15. The catheter of claim 11 wherein the reservoir extends along a length of the catheter shaft to a proximal reservoir port proximate to the proximal end of the catheter shaft.

16. A method of administering a bolus of fluid at a cardiovascular treatment site comprising:
   providing an elongate flexible catheter having a proximal and a distal end and a flexible elongate member slideably disposed in a lumen to form a bolus chamber at the distal end of the catheter;
   transluminally advancing the flexible catheter to a cardiovascular treatment site;
   proximally retracting the flexible elongate member to fill the bolus chamber through a catheter lumen opening at the distal end of the catheter; and
   distally advancing the flexible elongate member to express the bolus of fluid.

17. The method of claim 16 wherein the catheter includes a bolus reservoir containing the bolus in liquid communication with the lumen and comprising the step of charging the catheter with a bolus of liquid from the bolus reservoir.

18. The method of claim 17 and further comprising the step of:
   introducing the bolus into the reservoir prior to positioning of the distal end of the catheter at the treatment site.

19. The method of administering a bolus of fluid of claim 16 wherein the distal catheter lumen opening is fluidly coupled to a bolus reservoir.

20. A method comprising the steps of:
   intravascularly steering a catheter using a guidewire extending through a first lumen of the catheter to a treatment site;
   advancing a flexible elongate member slideably disposed in a second lumen of the catheter to express a bolus of material from a distal end of the catheter shaft.

21. A method of administering a bolus at a treatment site comprising the steps of:
   providing an elongate flexible catheter having a proximal end and a distal end and a flexible elongate member slideably disposed in a lumen of the catheter to form a bolus chamber at the distal end of the catheter;
   transluminally advancing the catheter using a visualization of the catheter to a treatment site;
   charging the bolus chamber of the catheter after transluminally advancing the catheter to the treatment site; and
   distally advancing the flexible elongate member to express the bolus.

22. A method of administering a bolus of material at a treatment site comprising the steps of:
   providing a catheter comprising: an elongate flexible catheter shaft having a proximal end, a distal end and a lumen extending therethrough; a flexible elongate member sideably disposed in the lumen of the catheter shaft and having a distal end spaced from a distal end of the lumen in a retractable position to form a distal bolus chamber and slideable in the lumen to express a bolus; and a reservoir having a distal portion located proximate the bolus chamber and being configured to provide fluid communication between the reservoir and the bolus chamber;
   intravascularly inserting the flexible catheter through a guide catheter to a treatment site; and
   distally advancing the flexible elongate member to express the bolus of material.

* * * * *